US011324711B2

(12) United States Patent
Schmidt

(10) Patent No.: US 11,324,711 B2
(45) Date of Patent: May 10, 2022

(54) COMPOSITION AND USES FOR INFLUENCING HAIR GROWTH

(75) Inventor: Alfred Schmidt, Waldkirch (DE)

(73) Assignee: S.W. Patentverwertungs Limited, Birmingham (GB)

( * ) Notice: Subject to any disclaimer, the term of this patent is extended or adjusted under 35 U.S.C. 154(b) by 0 days.

(21) Appl. No.: 12/736,076

(22) PCT Filed: Mar. 6, 2009

(86) PCT No.: PCT/EP2009/001644
§ 371 (c)(1),
(2), (4) Date: Nov. 23, 2010

(87) PCT Pub. No.: WO2009/109402
PCT Pub. Date: Sep. 11, 2009

(65) Prior Publication Data
US 2011/0117218 A1 May 19, 2011

(30) Foreign Application Priority Data
Mar. 7, 2008 (DE) .................... 10 2008 012 988.7

(51) Int. Cl.
*A61K 31/215* (2006.01)
*A61K 36/42* (2006.01)
*A61K 36/31* (2006.01)
*A61K 36/25* (2006.01)
*A61Q 5/08* (2006.01)
*A61K 36/19* (2006.01)
*A61Q 7/02* (2006.01)
*A61K 45/06* (2006.01)
*A61K 36/13* (2006.01)
*A61K 36/889* (2006.01)
*A61K 36/32* (2006.01)
*A61K 36/48* (2006.01)
*A61Q 7/00* (2006.01)
*A61K 8/63* (2006.01)
*A61K 31/5685* (2006.01)
*A61K 36/185* (2006.01)
*A61K 8/9755* (2017.01)
*A61K 8/9789* (2017.01)
*A61K 8/9794* (2017.01)
*A61K 31/56* (2006.01)

(52) U.S. Cl.
CPC .............. *A61K 31/215* (2013.01); *A61K 8/63* (2013.01); *A61K 8/9755* (2017.08); *A61K 8/9789* (2017.08); *A61K 8/9794* (2017.08); *A61K 31/56* (2013.01); *A61K 31/5685* (2013.01); *A61K 36/13* (2013.01); *A61K 36/185* (2013.01); *A61K 36/19* (2013.01); *A61K 36/25* (2013.01); *A61K 36/31* (2013.01); *A61K 36/32* (2013.01); *A61K 36/42* (2013.01); *A61K 36/48* (2013.01); *A61K 36/889* (2013.01); *A61K 45/06* (2013.01); *A61Q 5/08* (2013.01); *A61Q 7/00* (2013.01); *A61Q 7/02* (2013.01); *A61K 2800/782* (2013.01)

(58) Field of Classification Search
CPC .......... A61K 31/215; A61K 8/63; A61K 8/97
See application file for complete search history.

(56) References Cited

U.S. PATENT DOCUMENTS

| 6,017,893 | A |   | 1/2000  | Segelman |
|-----------|---|---|---------|----------|
| 6,019,976 | A | * | 2/2000  | Bryant ........................... 424/727 |
| 6,020,327 | A | * | 2/2000  | Messenger ............. A61K 8/496 514/170 |
| 6,117,429 | A | * | 9/2000  | Bucci ............................. 424/729 |
| 6,358,541 | B1 |  | 3/2002  | Goodman |
| 6,599,540 | B1 | * | 7/2003  | Fabre et al. ................... 424/727 |
| 6,673,366 | B1 | * | 1/2004  | Curry ............................ 424/451 |
| 7,105,573 | B2 |  | 9/2006  | Krajcik et al. |
| 7,238,375 | B1 |  | 7/2007  | Perry |
| 7,629,005 | B2 |  | 12/2009 | Popp |
| 2001/0033849 | A1 | | 10/2001 | Di Pierro |
| 2002/0001633 | A1 | | 1/2002  | Revel |
| 2003/0165547 | A1 | | 9/2003  | Picard-Lesboueyries et al. |
| 2003/0198657 | A1 | * | 10/2003 | Menon et al. ................ 424/401 |

(Continued)

FOREIGN PATENT DOCUMENTS

CA    2064768      2/1991
CN    101128209    2/2008

(Continued)

OTHER PUBLICATIONS

Leschber G et al. "Influence of an aromatase inhibitor (4-acetoxy-4-androstene-3,17-dione) on experimentally induced iimpairment of spermatogenesis in immature rats." Andrologia. Nov. 1989-Dec. 21(6):529-534 abstract only.*

"Body Building: Thread Novedex (4-Hydroxyandrostenedione (Formestane))". Internet posting date: Feb. 29, 2004 [Retrieved from the Internet on: Mar. 16, 2012]. Retrieved from the Internet: <URL: http://forum.bodybuilding.com/showthread.php?t=233702&page=1>.*

"Saw palmetto" from University of Maryland Medical Center. Internet Archive Date: Apr. 26, 2007 [Retrieved from the Internet on: Mar. 16, 2012]. Retrieved from the Internet: <URL: http://web.archive.org/web/20070426124648/http://www.umm.edu/altmed/articles/saw-palmetto-000272.htm>.*

(Continued)

*Primary Examiner* — Amy L Clark
(74) *Attorney, Agent, or Firm* — Locke Lord LLP; Nicholas J. DiCeglie, Jr.

(57) ABSTRACT

The invention describes a combination of at least one aromatase inhibitor selected from the group of chemical-synthetic aromatase inhibitors and aromatase inhibition exhibiting extracts of soya beans and rapeseed, respectively, and at least one plant extract that contains one or more active ingredient substance(s) extracted from the plant, which is(are) selected from the group of 5α reductase type I and/or type II inhibitors and androgen receptor blockers, said combination being contained for example in a composition and having special properties for influencing hair growth. Uses of this combination are also described.

6 Claims, No Drawings

(56) References Cited

U.S. PATENT DOCUMENTS

| | | |
|---|---|---|
| 2004/0018991 A1 | 1/2004 | Schmidt et al. |
| 2004/0213859 A1 | 10/2004 | Zelickson |
| 2005/0065126 A1* | 3/2005 | Lee ............................ 514/167 |
| 2005/0153948 A1* | 7/2005 | Spilburg ..................... 514/171 |
| 2006/0246153 A1 | 11/2006 | Bombardelli et al. |
| 2007/0036742 A1* | 2/2007 | Roufs .................. A61K 8/342 424/74 |
| 2007/0066661 A1 | 3/2007 | Krajcik et al. |
| 2007/0148123 A1 | 6/2007 | Wieland et al. |

FOREIGN PATENT DOCUMENTS

| | | |
|---|---|---|
| DE | 43 30 597 | 3/1995 |
| DE | 101 27 897 | 12/2002 |
| EP | 0 163 490 | 12/1985 |
| EP | 0 204 877 | 12/1986 |
| EP | 0 293 837 | 12/1988 |
| EP | 1 700 617 | 9/2006 |
| FR | 2 791 255 | 9/2000 |
| FR | 2 888 725 | 1/2007 |
| JP | 60-215608 | 10/1985 |
| JP | 60215608 A * | 10/1985 |
| JP | 4-81563 | 12/1992 |
| JP | 06-219926 | 8/1994 |
| JP | 06219926 A * | 8/1994 |
| JP | 09100220 A * | 4/1997 |
| JP | 10-508828 | 9/1998 |
| JP | 11-092340 | 4/1999 |
| JP | 2000-256204 | 9/2000 |
| JP | 2002-322050 | 11/2002 |
| JP | 2003-528123 | 9/2003 |
| JP | 2004-502634 | 1/2004 |
| JP | 2004-244350 | 9/2004 |
| JP | 2007-051129 | 3/2007 |
| JP | 2007-230888 | 9/2007 |
| JP | 2009-532342 | 9/2009 |
| WO | WO-91/02516 | 3/1991 |
| WO | WO-96/08231 | 3/1996 |
| WO | WO-97/03639 | 2/1997 |
| WO | WO-98/33472 | 8/1998 |
| WO | WO-9833472 A1 * | 8/1998 ............... A61Q 9/00 |
| WO | WO 9833472 A1 * | 8/1998 ............... A61K 8/97 |
| WO | WO-99/21009 | 4/1999 |
| WO | WO-99/22728 | 5/1999 |
| WO | WO-00/56269 | 9/2000 |
| WO | WO-01/12206 | 2/2001 |
| WO | WO-01/39656 | 6/2001 |
| WO | WO-01/72266 | 10/2001 |
| WO | WO-02/30355 | 4/2002 |
| WO | WO 02051426 A2 * | 7/2002 ............. A61K 9/127 |
| WO | WO-03/013561 | 2/2003 |
| WO | WO-03/030887 | 4/2003 |
| WO | WO-2004/034820 | 4/2004 |
| WO | WO-2006/066323 | 6/2006 |
| WO | WO-2006/066354 | 6/2006 |
| WO | WO-2007/030341 | 3/2007 |
| WO | WO-2007/113851 | 10/2007 |

OTHER PUBLICATIONS

Davies et al. Br. J. Cancer (1992), 66, 139-142.*
(U1) Brodie et al. Steroids. vol. 38, Issue 6, Dec. 1981, pp. 693-702, abstract only.*
(V1) Tice, R. Saw Palmetto (Serenoa repens) and One of Its Constituent Sterols—Sitosterol [83-46-5], Prepared for Errol Zeiger, Ph.D. 78 pages. (Year: 1997).*
Ososki et al., "Phytoestrogens: a Review of the Present State of Research", Phytotherapy Research, 17, 845-869 (2003), XP008039293.
Brodie et al., "Aromatase Inhibition and Inactivation[1]", Clinical Cancer Research, vol. 7, 4343-4349, Dec. 2001 (Suppl.).
International Search Report dated Sep. 1, 2010 in corresponding PCT Application No. EP/2009/001644.
Brodie, "Aromatase inhibitors in the treatment of breast cancer", The Journal of Steroid Biochemistry and Molecular Biology, vol. 49, issues 4-6, Jun. 1994, pp. 281-287.
Goss et al., "Current perspectives on aromatase inhibitors in breast cancer", Journal of Clinical Oncology, 12(11), 1994, pp. 2460-2470, abstract.
Brodie et al., "Studies on the Mechanism of Estrogen Biosynthesis in the Rat Ovary-I*", Journal of Steroid Biochemistry, 1976, vol. 7, pp. 787-793.
Marsh et al., "Aromatase Inhibitors. Synthesis and Biological Activity of Androstenedione Derivatives", J. Med. Chem. 1985, 28, 788-795.
Chen et al., "Cutaneous Androgen Metabolism: Basic Research and Clinical Perspectives", The Journal of Investigative Dermatology, vol. 119, No. 5, Nov. 2002, pp. 992-1007.
Hoffmann et al., "Current understanding of androgenetic alopecia. Part I: Etiopathogenesis", European Journal of Dermatology, vol. 10, No. 4, 319-327, Jun. 2000, Articles FMC.
Sawaya et al., "Different Levels of 5α-Reductase Type I and II, Aromatase, and Androgen Receptor in Hair Follicles of Women and Men with Androgenetic Alopecia", The Journal of Investigative Dermatology, vol. 109, No. 3, Sep. 1997, pp. 296-300.
Dr. Duke's Phytochemical and Ethnobotanical Databases: Activity Searches: Plant with a specific activity Aromatase-inhibitor; 5-alpha-reductase-inhibitor; Plant Searches: Serenoa repens, Urtica dioica, URL: http://www.ars-grin.gov/duke, download on Dec. 2, 2008.
Duke's Phytochemical and Ethnobotanical Databases: Chemicals and their Biological Activities in: Glycine max (L.) Merr. (Fabaceae)—Soybean, URL: http://www.ars-grin.gov/cgibin/duke/farmacy2.pl, download on Aug. 4, 2010.
Brodie, "Overview of Recent Development of Aromatase Inhibitors[1]", Cancer Research, vol. 42, Aug. 1982, p. 3312s-3314s.
Jeong et al., "Inhibition of Aromatase Activity by Flavonoids", Arch Pharm Res vol. 22, No. 3, 1999, pp. 309-312.
Minina et al., Chemistry and Technology of Phytopreparation, Moscow, 2004, pp. 148, 191, 192, 203 (Russian) including concise explanation in English.
Sarwar et al., "Phytoestrogen Actions in the Breast and Uterus", Phytoestrogens and Health, 2002, p. 445, Jul. 31, 2012 from http://books.google.ru (English).
Notice of Reason for Rejection dated May 27, 2013 in corresponding Japanese Patent Application No. 2010-549063.
Kim et al., Aromatase and Sulfatase Inhibitors from Lepiota americana, Planta Med 2000; 66(1): 78-79 (Abstract only).
Minami et al., "Aromatase Inhibitory Activities of Standishinal and the Diterpenoids from the Bark of Thuja standishii", Planta Med 2002; 68(8): 742-745 (Abstract only).
Ganβer et al., "Aromatase Inhibitors from Urtica dioica Roots", Planta Med 1995; 61(2): 138-140 (Abstract only).
Filleur et al., "Antiproliferative, Anti-aromatase, Anti-17β-HSD and Antioxidant Activities of Lignans Isolated from Myristica argentea", Planta Med 2001; 67(8): 700-704 (Abstract only).
J. Hackett et al. Synthesis and characterization of azole isoflavone inhibitors of aromatase, Bioorganic & Medicinal Chemistry 13, 4063-4070, (2005).

* cited by examiner

COMPOSITION AND USES FOR INFLUENCING HAIR GROWTH

The present invention relates to a composition that is particularly suitable for influencing hair growth, as well as to uses related thereto.

For many decades the research of hormone-dependent hair growth has been dominated by androgens. To this day, the androgen-metabolism and the androgen receptors are targets of both, the systemic pharmacological influencing of hair growth in the medicine and of the local, cosmetic attempts to control hair growth. However, it has been known for a long time that also estrogens have a significant influence on the hair follicles with respect to growth and cycle. Namely via binding to the local estrogen receptors.

Accordingly, it could be observed that an increase in local estradiol levels via local estradiol administration resulted in an increase in body hair. An adverse observation could be made when administering locally estradiol to the skin of the head: Here, the increased estradiol level and the increased local estradiol activity, respectively, led to hair loss. Basis of positively influencing the growth of head hair is that each hair follicle constitutes a unique "microcosmos" having the ability of complete self-regeneration. This is based on the interactions of its epithelial and mesenchymal components. These interactions also relate to the local development and the interplay of the sex hormones. These mechanisms of course play an equal role for body hair, although partially acting against each other. In addition to their regulatory function within the hair follicle cycle, these factors likewise play an important role within the hair pigmentation.

The key concept is therefore that in principle estrogens and androgens have a direct hair growth modulation function and, in addition thereto, indirectly act by varying the expression of important hair growth modulating factors. It is a basis of this concept that the two essential enzymes for the genesis of the active sex hormones, aromatase for the conversion of testosterone to estradiol and 5α reductase (type I and type II) for the conversion of testosterone to dihydrotestosterone, are strongly expressed and active in the region of the hair follicles. The same is true for the expression of the estrogen receptors α and β and of the androgen receptors. This means that the skin not only has a protective and regulatory function, but that the skin in addition is an important endocrine organ.

In the past there have been proposals to use aromatase inhibitors as cosmetic means and for influencing the hair growth, as e.g. discussed in WO 96/08231 A.

In a series of documents, saw palmetto extracts (*Serenoa repens*) are mentioned, predominantly in connection with pharmaceutic-therapeutic concepts, see e.g. JP 2007 230888 A with regard to androgen independent cancer; US 2006 246153 A with regard to benign prostate hypertrophy (BPH); JP 2007 051129 A as a component of a composition for an antagonist of angiotensin III type receptor or as inhibitor of the angiotensin I converting enzyme; WO 03/030887 A for treatment of sexual disorders and erectile dysfunctions, respectively; U.S. Pat. No. 6,599,540 for prevention and/or treatment of prostate cancer; US 2002 001633 A for treatment of inter alia BPH and prostate cancer; DE 10 127897 for treatment of osteoporosis or related disorders; WO 01/39656 A for treatment of symptoms of the lower urinary tract (LUTS) and of BPH; FR 2791255 with regard to anti-androgenic effect of cosmetic and dermo-pharmaceutic compositions; JP 2000 256204 A with regard to a composition with increased prostatomegaly inhibiting effect; WO 99/21009 A for preparation of suitable saw palmetto extracts; WO 97/03639 for topical cosmetic skin applications; EP-A-0204877 as dermatological topic composition for the treatment of acne; respectively in combination with different active ingredients as well as carriers. Besides, further documents deal with hair applications, see e.g.

JP 2002 322050 A with a composition of saw palmetto extracts with cystine (raw material of hair), citric acid and theanine for activation of the hair root and for bringing about the hair growth via oral administration, US 2001 033849 A with cosmetic compositions comprising fatty acids and anti-androgene styrenes of saw palmetto extracts and/or *Cucurbita* seed (*Cucurbita pepo*), U.S. Pat. No. 6,019,976 with therapeutic formulations containing saw palmetto extracts, vitamin B6, vitamin B3, zinc salt and L-arginine for treatment of male baldness via topical hair application, JP 11 092340 A with a formulation of saw palmetto extracts and a specific amount of an oil-soluble component of *Allium sativum L.* for supporting the blood stream and with a subsequent expected improvement of a hair renewing effect, and, therefore, for the treatment or the prevention of male hair loss, JP 60 215608 A with a saw palmetto extract for a hair strengthening preparation, WO 03/013561 A with pharmaceutical and/or cosmetic compositions containing extracts of saw palmetto and *Vitis vinifera* as effective components for treatment and prophylaxis of hair loss, of dandruffs and seborrhea, as well as WO 98/33472 with saw palmetto extracts or components thereof for prevention and/or treatment of androgenic hair loss and/or hirsutismus.

WO 91/02516 A relates to the use of a coleus extract for skin pigmentation, wherein supplementary substances such as xanthine, theophiline, tyrosine, chinine, skin irritant agents, 5α reductase inhibitors and saw palmetto extracts can be used, however, said document discloses—with regard to document EP-A-0 293 837 that deals with influencing of melanocytes of hair roots and therefore with the treatment of the hair—that in particular with regard to the metabolism wide differences exist between melanocytes in hair follicles and melanocytes in the skin.

Other documents deal with attempts of influencing and in particular of inhibiting 5α reductase.

U.S. Pat. No. 7,238,375 B1 describes four complexes 1-4, wherein complexes 1-3 should prevent hair loss and complex 4 should bring about hair growth. A mixture of copper ions, palm extract (*Serenoa repens*), pygeum extract (*Pygeum africanum*), nettle extract (*Urtica dioica*), zinc, vitamin B6 and linolenic acid belongs to complex 2.

U.S. Pat. No. 7,105,573 B2 and US2007/0066661 A1 relate to further suggestions for treating hair loss and other diseases that are linked to hair follicles.

The article of W. CHEN et al., "Cutaneous Androgen Metabolism: Basic Research and Clinical Perspectives", J Invest Dermatol. Vol. 119, No. 5, November 2002, pp. 992-1007 describes the androgen metabolism of the skin in general; and R. HOFFMANN and R. HAPPLE, "Current understanding of androgenetic alopecia. Part I: Etiopathogenesis", Eur J Dermatol. Vol 10, No. 4, June 2000, pp. 319-327 give a general overview of the state of knowledge in androgenic alopecia (AGA), wherein both cited articles give an impression of the complex circumstances of the anatomic regions that are relevant for skin and hair phenomena.

M. E. SAWAYA M. E., "Different Levels of 5α-Reductase Type I and II, Aromatase, and Androgen Receptor in Hair Follicles of Women and Men with Androgenetic Alopecia", J Invest Dermatol. Vol. 109, No. 3, September 1997, pp. 296-300 report on differences in the occurrence of the androgen receptor and of steroid-converting enzymes (5α reductase, aromatase) in man and woman and speculate that this could be responsible for the different clinical picture of AGA in man and woman. A list of possible active ingredients that can be assigned to respective plants can be found at Dr. Duke's Phytochemical and Ethnobotanical Databases, URL:http://www.ars-grin.gov/duke.

As explained above, the influencing of the hair growth refers to a highly complex system. This is reflected in a correspondingly high complexity of biochemical analyses and suggestions for influencing them. Despite a multitude of attempts the hitherto existing approaches have not been able to develop a proper balance with regard to a differentiated local influencing of the leading metabolites such as estrogens (in particular estradiol) and androgens (in particular dihydrotestosterone), depending on whether the hair growth or the hair removal—and inhibiting of the re-growth of hair after epilation or depilation, respectively—dependent on the treated skin region, i.e. on the one hand skin of the head (scalp) and on the other hand skin of the body including face (in particular beard area), and dependent on whether women or men are affected. A satisfying differentiated solution for specifically influencing in man as well as in woman has not yet been found. In particular, a depigmentation of hair represents an unpredictable problem in influencing the hair growth.

Therefore, it is an object of the present invention to provide an improved composition for influencing the hair growth and the hair pigmentation.

According to the invention it has been surprisingly found that if at least one aromatase inhibitor, selected from the group of chemical-synthetic aromatase inhibitors and aromatase inhibition exhibiting extracts of soya beans and rapeseed, respectively, (component (i)), is combined with at least one plant extract (component (ii)) that contains one or more active ingredient substance(s) extracted from the plant, which is(are) selected from the group consisting of 5α reductase type I and/or type II inhibitors and androgen receptor blockers, not only a targeted controllable influencing of the hair growth is reached, but at the same time also the hair pigmentation is controlled. In this way, either a hair depigmentation in woman, or, on the other hand, protection against hair depigmentation in man, can be achieved.

The novel combination according to the invention is characterized by an advantageous targeted influenceability of the hair growth, dependent on whether hair growth or hair removal and inhibition of new growth of hair dependent on the region of the body (scalp/skin of the head or body/face/beard area), respectively, and dependent on whether women or men are affected. Thereby, it namely has been surprisingly found out that the combination according to the invention allows for a targeted and differentiated influencing of the metabolites that are essential to hair growth such as estradiol and dihydrotestosterone, based on the local circumstances—i.e. specific for bringing about hair growth on the skin of the head/scalp in man or woman and for hair removal and inhibition of new growth of hair after epilation or depilation on the body (including beard area), respectively, in man or woman—combined with the possibility of a favourable influencing of the hair pigmentation and in particular re-pigmentation of hair, and, therefore, a return to the natural hair color.

For the differentiated combined effect according to the invention it is important that an effective aromatase inhibition is effected fast and efficiently, which is why component (i) is on the one hand selected from the group of chemical-synthetic aromatase inhibitors and/or on the other hand from aromatase inhibition exhibiting extracts of soya beans and/or rapeseed, respectively.

As a chemical-synthetic aromatase inhibitor that can be used in the composition according to the invention a substance that is known to have this function can be used, cf. e. g. A. M. H. Brodie in: "J. Steorid Biochem. Molec. Biol.", Vol. 49, No. 4-6, pp. 281-287 (1994), as well as P. E. Goss and K. M. E. H. Gwyn in: "Journal of Clinical Oncology", Vol. 12, No. 11, pp. 2460-2470 (1994), and for detection of the aromatase inhibition see e.g. A. M. H. Brodie et al. in: "J. Steroid Biochem. Molec. Biol.", Vol. 7, pp. 787-793 (1976), and D. A. Marsh et al. in: "J. Med. Chem.", Vol. 28, pp. 788-795 (1985). Suitable aromatase inhibitors can for instance be selected from the following group of compounds:

Steroidale aromatase inhibitors:
4-hydroxyandrost-4-ene-3,17-dione (formestan and lentaron),
6-methyleneandrostra-1,4-diene-3,17-dione (exemestane),
10-(2-propynyl)estr-4-ene-3,17-dione (MDL 18962)
7-alpha substituted androstendione-derivatives
1,4,6-androstatriene-3,17-dione (ATD)
10-oxirane- and 10-thiirane-substituted androgens
10-propargylestr-4-ene-3,17-dione
10-propargylestr-4-ene-3,17-propionate-10-(2-propynyl)-derivative
13-retro-antiprogestine
14-alpha-hydroxy-4-androstene-3,6,17-trione (14-alpha-OHAT)
16- or 19-substituted androst-4-enes
19-(cyclopropylamino)-androst-4-ene-3,17-dione
19-(ethyldithio)-androst-4-ene-3,17-dione
19-oxiranyl- and 19-thiiranyl-steroids
19-thiomethyl- and 19-azido-androstenedione
1-methyl-androsta-1,4-diene-3,17-dione (atamestane)
2,2-dimethyl-4-hydroxy-4-androstene-3,17-dione
3-alpha-methoxyandrost-4-ene-6,17-dione
3-beta-hydroxyandrost-4-ene-6-one-derivative
3-deoxyandrogen-19-oxygenatederivatives of 3-oxo-17'beta-carboxamido-steroids
4-(phenylthio)-4-androstene-3,17-dione
4-(thio-substituted)-4-androstene-3,17-dione
4-acetoxy-4-androstene-3,17-dione
4-aminoandrostenedione
4-androsten-3,6,17-trione
4-hydroxyandrostenedione (4-OHA)
4-methoxy-4-androstene-3,17-dione
4-oxygenated androst-5-ene-17-one and their 7-oxo-derivatives
4-thiosubstituted derivatives of 4-androstene-3,17-dione
4-thiosubstituated-4-androstene-3,17-dione-derivatives
5-alpha-dihydronorethindrone (a metabolite of norethindrone)
5-alpha-reduced C19-steroids
5-alpha-androstan-17-ones with or without a carbonyl functionality at C-3 and/or C-6
6-alpha-7-alpha-cyclopropanederivatives of androst-4-ene
6-alpha-fluorotestosterone
6-beta-propynyl-substituted steroids
6,7-aziridinylsteroide and related compounds
6-alkylanalogs of delta 1,4,6-androgens
6-alkyl- and 6-arylandrost-4-ene-3,17-dione
6-alkylandrost-4-ene-3,17-dions of 7 alpha- and 7-beta-arylaliphatic-substituted androst-4-ene-3,17-diones 6-alkylandrosta-4,6-diene-3,17-dione and their 1,4,6-triene-analogs
6-alkyl-substituted androgens
6-phenylaliphatic-substituted C19-steroids with 1,4-diene-, 4,6-diene- or 1,4,6-triene-structure
6-bromoandrostenedione
6-hydroxyiminoandrostenedione
6-methyleneandrosta-1,4-diene-3,17-dione (FCE 24304)
6-methyleneandrosta-1,4-diene-3,17-dione (FCE 24304)
6-phenylaliphatic-substituted androst-4-ene-3,17-diones
6-substituted androst-4-ene-analogs
7-alpha-(4'-amino)phenylthio-4-androstene-3,17-dione
7-alpha-substituted androsta-1,4-diene-3,17-diones
7-alpha-substituted androstenediones
7-alpha-(4'-amino)phenylthio-4-androstene-3,17-dione
7-alpha-arylaliphatic androsta-1,4-diene-3,17-diones
7-alpha-substituted androstenediones
7-substituted 4,6-androstadiene-3,17-diones
7-substituted steroids
Androst-4-ene-3,6-dione derivatives
Androst-5-ene-7,17-dione 19-nor- and 5-beta-6-beta-epoxy-derivatives
A-or B-ring-substituted derivatives of androst-4-ene-3,6,17-trione
A-ring bridged steroids
Bromoacetoxy-4-androstene-3-one
delta-1,4,6-androgens
delta-4,6-androgens
epimeric 6-hydroperoxyandrostenediones
Estr-4-ene-3,17-dione (MDL 18 962),
Estr-4-ene-3,6,17-trione
Flavonoids
RU486
Non-steroidal aromatase inhibitors:
6-[(4-chlorophenyl)(1H-1,2,4-triazole-1-yl)-methyl]-1-methyl-1H-benzotriazole (vorazol),
2,2'-[5-(1H-1,2,4-triazole-1-yl methyl)-1,3-phenylene]bis(2-methylproprionitrile) (arimidex),
4-[1-(cyanophenyl)-1-(1,2,4-triazolyl)methyl]benzonitrile (letrozole),
{4-(5,6,7,8-tetrahydro-imidazo-[1,5a]-pyridine-5-yl) benzonitrile monohydrochlorid (fadrozole)
Pyridoglutethimide (rogletimide)
Aminogluthetimide
1,2-imidazolylmethylcyclopentanole-derivatives
1-[(benzofurane-2-yl)phenylmethyl]-triazoles and -tetrazoles
1-[benzofurane-2-yl)-phenylmethyl]-imidazoles (substituted)
1-(benzofurane-2-ylmethyl)imidazole of N,N-disubstituted-5-aminopyrimidine-derivatives
1-imidazolyl(alkyl)-substituted di- and tetrahydrochinolines
1-pentyl-3-(4-aminophenyl)pyrrolidine-2,5-dione
1-phenyl-3-azabicyclo[3.1.0]hexane-2,4-dione
1-phenyl-3-azabicyclo[3.1.0]hexane-2,4-dione and analogs
3-alkylated 3-(4-aminophenyl)piperidine-2,6-diones
3-cycloalkyl-substituted 3-(4-aminophenyl)piperidine-2,6-diones
3-ethyl-3-(4-pyridyl)piperidine-2,6- and 5-alkyl derivatives
3-ethyl-3-(4-pyridyl)piperidine-2,6-dione-analogs
4-amino-4H-1,2,4-triazole-derivatives
4-cyclohexylaniline
Aminoglutethimide
Benzimidazole- and imidazole-compounds
Delta-1,4-bisnorcholadiene acid
Delta-1-testolactone
Imidazole derivatives of pyrrolidonic and piperidonic imidazolyl-1,3,5-triazines
MR 20492 and MR 20494 (two indolizinone derivatives)
Pyridyl-substituted indanones, indanes and tetralines
Triazine derivative SEF19
Substituted pyridines
Testololactone
Further aromatase inhibitors:
8-bromo-cyclic adenosinemonophosphate
FR901537
Hexamethylmelamine derivative (SAE9)
Letrozole (CGS 20267)
Mefloquine
MPV-2213ad
N-n-octanoylnornicotine and further nornicotine derivates
Org 33201
R 76713 and R 76713
Sesquiterpenelactone
SH 489
TAN-931
Thyroidhormons
Tobakalkaloid derivatives
YM511

As to the labelling of said substances as well as to their availability, see e.g. "Rote Liste", Editio Cantor Verlag, Aulendorf (DE), 2003. As an alternative to the use of the aforementioned compounds, or as additional component, it is preferred to employ an extract of soya beans (*Glycine soya*), and even better a rapeseed extract (*Brassica campestris;* engl.: rapeseed), with regard to an effectiveness in aromatase inhibition on the one hand, and a well-tolerated treatment of skin regions for a preferred local and topic application of the composition on the other hand. The respective extracts of soya beans and/or of rapeseed can be obtained for the inventive use as aromoatase inhibitor component in such a way that fractions are obtained respectively by suitable extraction and, if applicable, selective separation and isolation of those components of soya beans and/or rapeseed and rapeseed oil exhibiting aromatase inhibition function. Extracts of soya beans and, even better, extracts of rapeseed, can in addition advantageously bring forth a 5α reductase inhibition property, which allows for an even more advantageous mode of action, as described below. The selective isolation of extract fractions having aromatase and/or 5α reductase inhibiting function can be verified by appropriate testing of the fractions for the respective inhibitory effect and can be collected accordingly, wherein in each case known specific inhibition assays can be used.

The inventive combination effect is achieved by further using at least one plant extract that contains an active ingredient substance extracted from a plant selected from the group consisting of 5α reductase type I and/or type II inhibitors and androgen receptor blockers. The application of said plant extract shows clear advantages for the inventive purpose compared to the application of single chemical-synthetic 5α reductase inhibitors and is preferred, e.g. because in this case, steroidal phytosteroles and/or flavanoids are obtained as particularly favorable inventive active ingredients and/or because, in this case, regularly a total mixture of structurally and, as the case may be, functionally, different active ingredients are obtained. Consequently, according to the invention, such a plant extract is particularly preferred that contains multiple active ingredient substances extracted from the plant, i.e. a mixture of active ingredients that are selected from the group consisting of 5α reductase type I and/or type II inhibitors and androgen receptor blockers.

Plant extracts that can be used within the scope of the present invention that have an effect in inhibiting the 5α reductase type I and/or type II, preferably both, type I and type II form, are particularly preferred extracts from the following plants, respectively alone or in combination: Saw palmetto extract (*Serenoa repens*); *Taxus chinensis* (Pilg.) Rehd., *Canarium pimela* Koenig, *Beteropanax fragrans* (Roxb.) Seem., *Andrographis paniculata* (Burm. f.) Nees, *Acer palmatum, Zosteraceae, Zostera* sp., *Yacon* (a natural plant originating from Peru, belonging to the genus of *Asteraceae*, botanical name: *Polyrmioa sonchifolia*), sesame, gooseberry (genus *Phyllanthus* of the family Euphorbiaceace, botan. name *Phyllanthus emblica*), *Striga asiatica* (L.) O. Kuntze, *Butea monosperma*(Lam.) Taub., *Alangium chinense* (Lour.) Harms, *Alternanthera sessilis* (L.) R. Br., *Procryis wightiana* wall ex Wedd, *Desmodium triflorum* (L.) DC., *Stephania japonica* Miers., *Polypodium vulgare, Quercus*-plant (genus), *Psidium guajava L, Plumbago zeylanicum L., Cyperus rotundus L., Ricinus communis L., Embelia ribes* Burm. f., *Jangkang, Daun trawas, Cuachalalat* (originates from the Acapulco region in the South of Mexico), *Piper methysticum* (genus *Piper,* family Piperaceae), *Impatiens balsamina L., Thuja orientalis* (family of the cypress), plants of the genus *Coriandrum* as e.g. *Corlandrum sativum L., Cassia auriculata* (in particular bark), *Quercus pedunculata* (in particular fruits), *Rumex cyprius, Sumilax zeylanica, Phyllanthus nuriri, Woodfordia fruticosa, Lagerstroemia speciosa, Cymbopogon nardus, Glycyrrhiza glabra* or *Rheum, Belamcanda chinensis DC.* (family Iridaceae), *Rosa rugosa Thunb, Saxifraga stolonifera Meerburg, Garcinia mangostana L., Nephelium lappaceum L., Pyrola japonica Klenza, Trichosanthes cucumeroides Maxim, Kadsura japonia Dunal, Cuscuta australis R. Br., Cuscuta japonica Choisy, Euchresta japonica Benth., Lilium makinoi Koidzumi, balbatimone, Rosaceae* such as peach, *Rosa rugasa, Rosa odorata, Rosa odorata, R. coptophyllus, Rosa centifolia, sanguisorba officinalis L.* or *Pseudocydonia siensis, Leguminosae, Polygoni multiflori radix, Chaenomelis fructus, Zanthoxylic fructus, Thujae orientalis, Landium domesticum Jack* var. Duku (Duku) or *Landiurn domesticum Jack* var. Langsat (Langsat) of the family Meliaceae, *Uncaria gambir*, fennel, polygala, liquorice, pharbitis, plantane, clove, arecanuts, kolophonium, *Stachys betonica*, Geranium herb, Pounellae spical, Bupleurum elatum, Artenisiae capillaris Flos, Rosae fructus, Coicis semen, Nepetae herba, Dichroa, Valeriana officinalis.

Plant extracts that can be used within the scope of the present invention that have an effect in blocking the androgen receptor (anti-androgen) are preferred, in particular the following extracts, respectively alone or in combination:

*Chromolaena odoratum* (L.) K. R., coconut oil, Cuban king palm (*Roystonea regia*), *Pygeum africanum, Serenoa repens, Cucurbita pepo, Albizia lebbeck* (L.) *Benth* (from bark), *Roystonea regia* (from fruits), *Ruta graveolens L, Azadirachta indica A. Juss* (from leaves), *Momordica charantia* (from seeds), *Ganoderma lucidum, Echinacea purpurea, Belamcanda chinensis, Citrus aurantium, Echinacea purpurea, Silybum marianum* (milk thistle), *Crotalaria juncea Linn, Pygeum africanum*, pumpkin seed oil, crimson clover (in particular, flavanoid-rich components; *Trifoleum pratense*) pine (*Pinus*), spruce (*Picea*), rye (flower pollen extract), soya,

*Pygeum africanum, Hypoxis rooperi* (root), stinging nettle (*Urtica dioica*), *Cordia multispicata* (Triterpenoid extract) from Brazil, *Myricae cortex* (*Myrica rubra* Sieb. et Zucc., *Myricaceae,* from bark), *Pygeum africanum* (Tadenan; bark extract from the African plum), *Azadirachta indica, Sophora flavescens, Hibiscus rosa sinesis, Dalbergia cochinchinensis, Fructus psoraleae, Striga orobanchioides,* and *Vitex negundo* (from seed).

Extracts of fruits of the saw palmetto (*Serona serrulata* fruit extract) (in particular the ethanol extract), of pumpkin seeds, stinging nettle, *Taxus chinensis* (Pilg.) Rehd., *Canarium pimela* Koenig, *Heteropanax fragrans* (Roxb.) Seem. and *Andrographis paniculata* (Burm.f.) Nees are particularly preferred used as they inhibit the 5α reductase (type I and type II) and at the same time allow for a blockade of androgen receptors.

In general, the extract can be obtained from the whole plant or a part thereof, e.g. from leaves, stems or branches, from the bark, flowers, fruits, roots or the like. Preferably, prior to the extraction, the plant source is grinded, crushed or pulverized. Further optional processing steps are heating, refluxing, filtration, concentration, spray drying, freeze-drying. Preferably, a specific isolation step separating the extracted sample e.g. by using appropriate chromatographic methods, and isolating the respective fractions with the desired effect and, as the case may be, further purifying, is added. By doing so, for instance the isolation of the target can take place by determining and verification of the respective desired activity, and/or by testing for a substantial content of flavanoids and/or preferably of phytosterols, in particular of beta-sitosterol, stigmasterol and campesterol. Particularly preferred, the plant extract of component (ii) represents an extract being rich in phytosterols and/or flavanoids, i.e. the proportion of phytosterols and/or flavanoids based on the total plant extract of component (ii) is e.g. at least 50% by weight, further preferred at least 75% by weight and in particular at least 90% by weight.

In order to predominantly isolate the preferred steroidal active ingredients from the mentioned plants, they are preferably extracted with organic solvents, e.g. with methanol, ethanol, hexanol, glycol, such as ethylene glycol or 1,3-butyleneglycol, acetone, hexane, benzene, toluene, chloroform. A particularly preferred extracting agent is ethanol.

According to the invention, it is particularly preferred if either component (i) or component (ii), even better at the same time both components, inhibit(s) the type I or the type II 5α reductase and, further preferred, both isoforms, in order to allow for a multifunctional mechanism of action without having to admix further active substances and therefore potentially generating unpleasant side-effects. Hereby, an optimized combination of active substances that is in particular characterized by a beneficial influencing of the positive hair growth of the head hair with the possibility of a re-pigmentation of the hair by an otherwise strong pushing back of the hair growth of the body hair (as well as for the so called "facial hair on the chin and upper lip of women" (in German: "Damenbart") is obtained, provided that only the aromatase inhibtor—in the form of one or more of the chemical substances mentioned above and/or in the form of a soya bean extract or of a rapeseed extract—as active principle is combined with the plant extract of component (ii) and in particular with a saw palmetto extract, without adding further pharmacological active substances, but only suitable carriers, excipients or additives, depending on the desired formulation. This is in particular the case when an aromatase inhibitor is used that inhibits the aromatase by covalent binding to the aromatase, in particular when using 4-hydroxy-androstenedione, 4-acetoxy-andostenedione or a 4-ester-derivative thereof, wherein the ester group can contain common alkyl groups such as methyl-, acetyl-, n- or iso-propyl-, n-, sec- or t-butyl ester.

It is assumed that when using component (i) having aromatase inhibition, preferably selected from 4-hydroxy-androstenedione, 4-acetoxy-andostenedione, a 4-carboxylic acid ester derivative thereof, soya bean extract and rapeseed extract, each with aromatase inhibition effect, in combination with the plant extract of component (ii), a multi-modal mechanism of action is carried out, namely apart from the inhibition of the aromatase at the same time an inhibition of the 5α reductase (type I and type II) and, in addition thereto, a blockage of the androgen receptors, without the requirement of further, as the case may be unpleasant, additives of active ingredients.

The amounts of the above mentioned active substance components—i.e. each aromatase inhibtor, saw palmetto extract and, as the case may be, additional 5α reductase inhibitor—are for example, each independently, ranges of from 0.0001 to 50% by weight, preferably of from 0.001 to 20% by weight, further preferred of from 0.01 to 10% by weight, and in particular of from 0.1 to 5% by weight, respectively based on the total composition.

In addition to the above-mentioned active ingredients, the composition according to the invention can contain conventional carriers, excipients or additives. In particular, such additives are possible that are suitable for topical routes of administration. Additives include for instance vegetable oils such as almond oil, olive oil, peach kernel oil, peanut oil, castor oil and the like, plant extracts, essential oils, vitamin oils, lipids and lipid-like substances, lipoids, phosphotides, hydrocarbons such as paraffins, petrolatum, lanolin, waxes and the like, detergents, further skin active agents such as lecithine, wool fat, carotene and the like, skin nutrients, perfumes, cosmetic substances, alcohols, water and water mixtures, glycerol, glycol, urea, talc, preservatives, sunscreens, colorants such as titanium white and zinc white, and anti-oxidants or the like, as well as mixtures of said substances, however without being restricted thereto. In general, water serves as basic substance, so that—conventionally by the addition of emulsifiers such as fatty alcohol sulphate, alkali soaps, lecithines, triethanolamine and the like—an O/W- or W/O-emulsion is obtained. Commercially available, conventional skin care products are also applicable as base mixture in addition to the active substances. Suitable types of formulations for the composition according to the invention are for instance an ointment, a cream, a gel, an emulsion, a lotion, a spray, a powder, an oil or the like. Preferably, the composition according to the invention is however free of harmful, undesired or even toxic additives, in particular is free of metallic additives such as copper.

In the following, the invention is discussed in more detail by means of the following examples that are however not to be understood in a limiting way. Data in percent mean percent by weight of the respective composition.

EXAMPLES 1-8

In the following Examples 1-8, the given ingredients (active ingredients and mixtures of active ingredients, respectively) for preparation of tinctures for influencing the hair growth were respectively applied to men and women.

Hair Growth Head Men:

Example 1

AQUA 14.24%, DIMETHYL ISOSORBIDE 10%, SERENOA SERRULATA FRUIT EXTRACT 0.99%, 4-HYDROXY-ANDROSTENEDIONE 0.6%, *URTICA DIOICA* (NETTLE) EXTRACT 1%, *TUSSILAGO FARFARA* (COLTSFOOT) LEAF EXTRACT 0.2%, RETINYL PALMITATE 0.05%, TOCOPHEROL 0.02%, ZINC PCA 0.2%, *EQUISETUM ARVENSE* EXTRACT 0.2%, *MALVA SYLVESTRIS* (MALLOW) EXTRACT 0.4%, DISODIUM CYSTINYL DISUCCINATE 0.2%, PIROCTONE OLAMINE 0.2%, TRIDECYL SALICYLATE 0.2%, NIACINAMIDE 0.1%, *HAMAMELIS VIRGINIANA* (WITCH HAZEL) EXTRACT 0.4%, *OLEA EUROPAEA* (OLIVE) OIL UNSAPONIFIABLES 0.4%, BIOTIN 0.2%, UREA 0.25%, PEG-40 HYDROGENATED CASTOR OIL 0.05%, PROPYLENE GLYCOL 0.05%, LACTIC ACID 0.05%, and rest ALCOHOL DENAT. (70%).

Example 2

AQUA 14.24%, DIMETHYL ISOSORBIDE 10%, *SERENOA SERRULATA* FRUIT EXTRACT 0.99%, ACETOXYANDROSTENEDIONE 0.6%, *URTICA DIOICA* (NETTLE) EXTRACT 1%, *TUSSILAGO FARFARA* (COLTSFOOT) LEAF EXTRACT 0.2%, RETINYL PALMITATE 0.05%, TOCOPHEROL 0.02%, ZINC PCA 0.2%, *EQUISETUM ARVENSE* EXTRACT 0.2%, *MALVA SYLVESTRIS* (MALLOW) EXTRACT 0.4%, DISODIUM CYSTINYL DISUCCINATE 0.2%, PIROCTONE OLAMINE 0.2%, TRIDECYL SALICYLATE 0.2%, NIACINAMIDE 0.1%, *HAMAMELIS VIRGINIANA* (WITCH HAZEL) EXTRACT 0.4%, *OLEA EUROPAEA* (OLIVE) OIL UNSAPONIFIABLES 0.4%, BIOTIN 0.2%, UREA 0.25%, PEG-40 HYDROGENATED CASTOR OIL 0.05%, PROPYLENE GLYCOL 0.05%, LACTIC ACID 0.05%, and rest ALCOHOL DENAT. (70%).

Example 3

AQUA 14.33%, DIMETHYL ISOSORBIDE 10%, *SERENOA SERRULATA* FRUIT EXTRACT 1%, *GLYCINE SOYA* (SOYBEAN) STEROLS 0.5%, *URTICA DIOICA* (NETTLE) EXTRACT 1%, *TUSSILAGO FARFARA* (COLTSFOOT) LEAF EXTRACT 0.2%, RETINYL PALMITATE 0.05%, TOCOPHEROL 0.02%, ZINC PCA 0.2%, *EQUISETUM ARVENSE* EXTRACT 0.2%, *MALVA SYLVESTRIS* (MALLOW) EXTRACT 0.4%, DISODIUM CYSTINYL DISUCCINATE 0.2%, PIROCTONE OLAMINE 0.2%, TRIDECYL SALICYLATE 0.2%, NIACINAMIDE 0.1%, *HAMAMELIS VIRGINIANA* (WITCH HAZEL) EXTRACT 0.4%, *OLEA EUROPAEA* (OLIVE) OIL UNSAPONIFIABLES 0.4%, BIOTIN 0.2%, UREA 0.25%, PEG-40 HYDROGENATED CASTOR OIL 0.05%, PROPYLENE GLYCOL 0.05%, LACTIC ACID 0.05%, and rest ALCOHOL DENAT. (70%).

Example 4

AQUA 14.33%, DIMETHYL ISOSORBIDE 10%, *SERENOA SERRULATA* FRUIT EXTRACT 1%, *BRASSICA CAMPESTRIS* (RAPESEED) STEROLS 0.5%, *URTICA DIOICA* (NETTLE) EXTRACT 1%, *TUSSILAGO FARFARA* (COLTSFOOT) LEAF EXTRACT 0.2%, RETINYL PALMITATE 0.05%, TOCOPHEROL 0.02%, ZINC PCA 0.2%, *EQUISETUM ARVENSE* EXTRACT 0.2%, *MALVA SYLVESTRIS* (MALLOW) EXTRACT 0.4%, DISODIUM CYSTINYL DISUCCINATE 0.2%, PIROCTONE OLAMINE 0.2%, TRIDECYL SALICYLATE 0.2%, NIACINAMIDE 0.1%, *HAMAMELIS VIRGINIANA* (WITCH HAZEL) EXTRACT 0.4%, *OLEA EUROPAEA*

(OLIVE) OIL UNSAPONIFIABLES 0.4%, BIOTIN 0.2%, UREA 0.25%, PEG-40 HYDROGENATED CASTOR OIL 0.05%, PROPYLENE GLYCOL 0.05%, LACTIC ACID 0.05%, and rest ALCOHOL DENAT. (70%).

Hair Growth Head Women:

Example 5

AQUA 14.33%, DIMETHYL ISOSORBIDE 10%, 4-HYDROXY-ANDROSTENEDIONE 0.7%, *SERENOA SERRULATA* FRUIT EXTRACT 0.8%, *URTICA DIOICA* (NETTLE) EXTRACT 1%, *TUSSILAGO FARFARA* (COLTSFOOT) LEAF EXTRACT 0.2%, RETINYL PALMITATE 0.05%, TOCOPHEROL 0.02%, ZINC PCA 0.2%, *EQUISETUM ARVENSE* EXTRACT 0.2%, *MALVA SYLVESTRIS* (MALLOW) EXTRACT 0.4%, DISODIUM CYSTINYL DISUCCINATE 0.2%, PIROCTONE OLAMINE 0.2%, TRIDECYL SALICYLATE 0.2%, NIACINAMIDE 0.1%, *HAMAMELIS VIRGINIANA* (WITCH HAZEL) EXTRACT 0.4%, *OLEA EUROPAEA* (OLIVE) OIL UNSAPONIFIABLES 0.4%, BIOTIN 0.2%, UREA 0.25%, PEG-40 HYDROGENATED CASTOR OIL 0.05%, PROPYLENE GLYCOL 0.05%, LACTIC ACID 0.05, and rest ALCOHOL DENAT. (70%).

Example 6

AQUA 14.33%, DIMETHYL ISOSORBIDE 19%, ACETOXYANDROSTENEDIONE 0.7%, *SERENOA SERRULATA* FRUIT EXTRACT 0.8%, *URTICA DIOICA* (NETTLE) EXTRACT 1%, *TUSSILAGO FARFARA* (COLTSFOOT) LEAF EXTRACT 0.2%, RETINYL PALMITATE 0.05%, TOCOPHEROL 0.02%, ZINC PCA 0.2%, *EQUISETUM ARVENSE* EXTRACT 0.2%, *MALVA SYLVESTRIS* (MALLOW) EXTRACT 0.4%, DISODIUM CYSTINYL DISUCCINATE 0.2%, PIROCTONE OLAMINE 0.2%, TRIDECYL SALICYLATE 0.2%, NIACINAMIDE 0.1%, *HAMAMELIS VIRGINIANA* (WITCH HAZEL) EXTRACT 0.4%, *OLEA EUROPAEA* (OLIVE) OIL UNSAPONIFIABLES 0.4%, BIOTIN 0.2%, UREA 0.25%, PEG-40 HYDROGENATED CASTOR OIL 0.05%, PROPYLENE GLYCOL 0.05%, LACTIC ACID 0.05%, and rest ALCOHOL DENAT. (70%).

Example 7

AQUA 14.23%, DIMETHYL ISOSORBIDE 10%, *GLYCINE SOYA* (SOYBEAN) STEROLS 1%, *SERENOA SERRULATA* FRUIT EXTRACT 0.6%, *URTICA DIOICA* (NETTLE) EXTRACT 1%, *TUSSILAGO FARFARA* (COLTSFOOT) LEAF EXTRACT 0.2%, RETINYL PALMITATE 0.05%, TOCOPHEROL 0.02%, ZINC PCA 0.2%, *EQUISETUM ARVENSE* EXTRACT 0.2%, *MALVA SYLVESTRIS* (MALLOW) EXTRACT 0.4%, DISODIUM CYSTINYL DISUCCINATE 0.2%, PIROCTONE OLAMINE 0.2%, TRIDECYL SALICYLATE 0.2%, NIACINAMIDE 0.1%, *HAMAMELIS VIRGINIANA* (WITCH HAZEL) EXTRACT 0.4%, *OLEA EUROPAEA* (OLIVE) OIL UNSAPONIFIABLES 0.4%, BIOTIN 0.2%, UREA 0.25%, PEG-40 HYDROGENATED CASTOR OIL 0.05%, PROPYLENE GLYCOL 0.05%, LACTIC ACID 0.05%, and rest ALCOHOL DENAT. (70%).

Example 8

AQUA 14.23%, DIMETHYL ISOSORBIDE 10%, *BRASSICA CAMPESTRIS* (RAPESEED) STEROLS 1%, *SERENOA SERRULATA* FRUIT EXTRACT 0.6%, *URTICA DIOICA* (NETTLE) EXTRACT 1%, *TUSSILAGO FARFARA* (COLTSFOOT) LEAF EXTRACT 0.2%, RETINYL PALMITATE 0.05%, TOCOPHEROL 0.02%, ZINC PCA 0.2%, *EQUISETUM ARVENSE* EXTRACT 0.2%, *MALVA SYLVESTRIS* (MALLOW) EXTRACT 0.4%, DISODIUM CYSTINYL DISUCCINATE 0.2%, PIROCTONE OLAMINE 0.2%, TRIDECYL SALICYLATE 0.2%, NIACINAMIDE 0.1%, *HAMAMELIS VIRGINIANA* (WITCH HAZEL) EXTRACT 0.4%, *OLEA EUROPAEA* (OLIVE) OIL UNSAPONIFIABLES 0.4%, BIOTIN 0.2%, UREA 0.25%, PEG-40 HYDROGENATED CASTOR OIL 0.05%, PROPYLENE GLYCOL 0.05%, LACTIC ACID 0.05%, and rest ALCOHOL DENAT. (70%).

EXAMPLES 9-14

In the following Examples 9-14, said ingredients for preparation of creams for influencing the re-growth of hair and the removal of hair (face and body) were used.

Hair Removal Body:

Example 9

DIMETHYL ISOSORBIDE 6%, *PERSEA GRATISSIMA* (AVOCADO) OIL 4%, OCTYLDODECANOL 3.9%, TRIDECYL SALICYLATE 2%, C12-13 ALKYL LACTATE 2%, CETEARYL ISONONANOATE 2%, CAPRYLIC/CAPRIC TRIGLYCERIDE 1.9476%, POLYGLYCERYL-3 METHYLGLUCOSE DISTEARATE 1.9%, AMMONIUM ACRYLOYLDIMETHYLTAURATE/VP CO POLYMER 0.85%, *SERENOA SERRULATA* FRUIT EXTRACT 0.9%, *BRASSICA CAMPESTRIS* (RAPESEED) STEROLS 0.5%, *GLYCINE SOYA* (SOYBEAN) STEROLS 0.5%, TOCOPHERYL ACETATE 0.9%, TOCOPHEROL 0.0175%, CAPRYLOYL GLYCINE 0.1%, TRIBEHENIN 0.9%, GLYCERIN 0.9552%, XYLITOL 0.9%, SORBITOL 0.9%, PALMATINE 0.0024%, COCO-GLUCOSIDE 0.052%, ETHYLHEXYLGLYCERIN 0.3%, LACTIC ACID 0.12%, SORBITAN LAURATE 0.09%, POLOXAMER 407 0.5%, NYLON-12 0.06%, LECITHIN 0.028%, ASCORBYL PALMITATE 0.0175%, AMMONIA 0.0175, PHENOXYETHANOL 0.8%, XANTHAN GUM 0.1%, and rest AQUA (66.7423%).

Example 10

DIMETHYL ISOSORBIDE 6%, *PERSEA GRATISSIMA* (AVOCADO) OIL 4%, OCTYLDODECANOL 3.9%, TRIDECYL SALICYLATE 2%, C12-13 ALKYL LACTATE 2%, CETEARYL ISONONANOATE 2%, CAPRYLIC/CAPRIC TRIGLYCERIDE 1.9476%, POLYGLYCERYL-3 METHYLGLUCOSE DISTEARATE 1.9%, AMMONIUM ACRYLOYLDIMETHYLTAURATE/VP COPOLYMER 0.85%, *SERENOA SERRULATA* FRUIT EXTRACT 0.9%, ACETOXYANDROSTENEDIONE 0.5%, TOCOPHERYL ACETATE 0.9%, TOCOPHEROL 0.0175%, CAPRYLOYL GLYCINE 0.1%, TRIBEHENIN 0.9%, GLYCERIN 0.9552%, XYLITOL 0.9%, SORBITOL 0.9%, PALMATINE 0.024%, COCO-GLUCOSIDE 0.052%, ETHYLHEXYLGLYCERIN 0.3%, LACTIC ACID 0.12%, SORBITAN LAURATE 0.09%, POLOXAMER 407 0.5%, NYLON-12 0.06%, LECITHIN 0.028%, ASCORBYL PALMITATE 0.0175%, AMMONIA 0.0175%, PHENOXYETHANOL 0.8%, XANTHANGUM 0.1%, and rest AQUA (67.2423%).

Example 11

DIMETHYL ISOSORBIDE 6%, PERSEA GRATISSIMA (AVOCADO) OIL 4%, OCTYLDODECANOL 3.9%, TRIDECYL SALICYLATE 2%, C12-13 ALKYL LACTATE 2%, CETEARYL ISONONANOATE 2%, CAPRYLIC/CAPRIC TRIGLYCERIDE 1.9476%, POLYGLYCERYL-3 METHYLGLUCOSE DISTEARATE 1.9%, AMMONIUM ACRYLOYLDIMETHYLTAURATE/VP COPOLYMER 0.85%, SERENOA SERRULATA FRUIT EXTRACT 0.9%, 4-HYDROXY-ANDROSTENEDIONE 0.5%, TOCOPHERYL ACETATE 0.9%, TOCOPHEROL 0.0175%, CAPRYLOYL GLYCINE 0.1%, TRIBEHENIN 0.9%, GLYCERIN 0.9552, XYLITOL 0.9%, SORBITOL 0.9%, PALMATINE 0.024%, COCO-GLUCOSIDE 0.052%, ETHYLHEXYLGLYCERIN 0.3%, LACTIC ACID 0.12%, SORBITAN LAURATE 0.09%, POLOXAMER 407 0.5%, NYLON-12 0.06%, LECITHIN 0.028%, ASCORBYL PALMITATE 0.0175%, AMMONIA 0.0175, PHENOXYETHANOL 0.8%, XANTHAN GUM 0.1%, and rest AQUA (67.2423%).

Hair Removal Face:

Example 12

DIMETHYL ISOSORBIDE 6%, PERSEA GRATISSIMA (AVOCADO) OIL 4.5%, OCTYLDODECANOL 4.4%, TRIDECYL SALICYLATE 2%, C12-13 ALKYL LACTATE 2%, CETEARYL ISONONANOATE 2%, CAPRYLIC/CAPRIC TRIGLYCERIDE 1.9476%, POLYGLYCERYL-3 METHYLGLUCOSE DISTEARATE 1.9%, BRASSICA CAMPESTRIS (RAPESEED) STEROLS 0.5%, GLYCINE SOYA (SOYBEAN) STEROLS 0.48%, SERENOA SERRULATA FRUIT EXTRACT 0.9%, CAPRYLOYL GLYCINE 0.1%, TRIBEHENIN 0.9%, GLYCERIN 0.9552%, XYLITOL 0.9%, SORBITOL 0.9%, AMMONIUM ACRYLOYLDIMETHYLTAURATE/VP COPOLYMER 1.25%, PALMATINE 0.024%, COCO-GLUCOSIDE 0.052%, TOCOPHERYL ACETATE 0.9%, TOCOPHEROL 0.0175%, ETHYLHEXYLGLYCERIN 0.3%, LACTIC ACID 0.12%, SORBITAN LAURATE 0.09%, POLOXAMER 407 0.5%, NYLON-12 0.06%, LECITHIN 0.028%, ASCORBYL PALMITATE 0.0175%, AMMONIA 0.0175%, PHENOXYETHANOL 0.8%, XANTHAN GUM 0.1%, and rest AQUA (65.3407%).

Example 13

DIMETHYL ISOSORBIDE 6%, PERSEA GRATISSIMA (AVOCADO) OIL 4.5%, OCTYLDODECANOL 4.4%, TRIDECYL SALICYLATE 2%, C12-13 ALKYL LACTATE 2%, CETEARYL ISONONANOATE 2%, CAPRYLIC/CAPRIC TRIGLYCERIDE 1.9476%, POLYGLYCERYL-3 METHYLGLUCOSE DISTEARATE 1.9%, ACETOXYANDROSTENEDIONE 0.68, SERENOA SERRULATA FRUIT EXTRACT 0.9%, CAPRYLOYL GLYCINE 0.1%, TRIBEHENIN 0.9%, GLYCERIN 0.9552%, XYLITOL 0.9%, SORBITOL 0.9%, AMMONIUM ACRYLOYLDIMETHYLTAURATE/VP CO POLYMER 1.25%, PALMATINE 0.024%, COCO-GLUCOSIDE 0.52%, TOCOPHERYL ACETATE 0.9%, TOCOPHEROL 0.0175%, ETHYLHEXYLGLYCERIN 0.3%, LACTIC ACID 0.12%, SORBITAN LAURATE 0.09%, POLOXAMER 407 0.5%, NYLON-12 0.06%, LECITHIN 0.028%, ASCORBYL PALMITATE 0.0175%, AMMONIA 0.0175%, PHENOXYETHANOL 0.8%, XANTHAN GUM 0.1%, and rest AQUA (65.6407%).

Example 14

DIMETHYL ISOSORBIDE 6%, PERSEA GRATISSIMA (AVOCADO) OIL 4.5%, OCTYLDODECANOL 4.4%, TRIDECYL SALICYLATE 2%, C12-13 ALKYL LACTATE 2%, CETEARYL ISONONANOATE 2%, CAPRYLIC/CAPRIC TRIGLYCERIDE 1.9476%, POLYGLYCERYL-3 METHYLGLUCOSE DISTEARATE 1.9%, 4-HYDROXY-ANDROSTENEDIONE 0.68%, SERENOA SERRULATA FRUIT EXTRACT 0.9%, CAPRYLOYL GLYCINE 0.1%, TRIBEHENIN 0.9%, GLYCERIN 0.9552%, XYLITOL 0.9%, SORBITOL 0.9%, AMMONIUM ACRYLOYLDIMETHYLTAURATE/VP CO POLYMER 1.25%, PALMATINE 0.024%, COCO-GLUCOSIDE 0.052%, TOCOPHERYL ACETATE 0.9%, TOCOPHEROL 0.0175%, ETHYLHEXYLGLYCERIN 0.3%, LACTIC ACID 0.12%, SORBITAN LAURATE 0.09%, POLOXAMER 407 0.5%, NYLON-12 0.06%, LECITHIN 0.028%, ASCORBYL PALMITATE 0.0175%, AMMONIA 0.0175%, PHENOXYETHANOL 0.8%, XANTHAN GUM 0.1%, and rest AQUA (65.6407%).

The following application Examples 1 and 2 illustrate the results obtained with representatively selected compositions of preparation Examples (1-14) in cases with problems of hair growth and with excess hairiness on body and face, respectively.

APPLICATION EXAMPLES 1 AND 2

Application Example 1

Influence on the Head Hair in Women and Men With Genetic Alopecia

In 10 women aged between 40 and 60 years and in 12 men aged between 34 and 64 with severe genetic alopecia lotio preparations with the following combinations of active ingredients were applied:

In women: A lotion having the composition according to Example 6 (n=4) and according to Example 5 (n=6), respectively.

In men: A lotion having the composition according to Example 2 (n=12).

Results:

Already after 3 months, all men and women exhibited both a positive influence on the hair growth (amount of hair) and an increase in the thickness of the hair. In addition to an extremely remarkable increase in hair growth (amount of hair), after 6 months a considerable increase in the thickness of the hair appeared. Surprisingly, nearly all women (n=9) and nearly all men (n=10) exhibited a re-pigmentation of the hair and, therefore, a return to the original hair color.

Application Example 2

Excessive Hair Growth on the Legs (n=35) and So-Called "Facial Hair on the Chin and Upper Lip of Women" (in German: "Damenbart") (n=6) in Women Application to the Hair Growth on the Legs in Women:

For 6 months, women exhibiting a strong hair growth on the legs (n=35) have been given a cream having the composition according to Example 10 (N=15) or Example 11 (n=20).

Results:

The examination covered 180 days with examination time points in 30-day intervals. The results were surprising. A reduction of the amount and thickness of hair could be detected already after 30 days. After 180 days, the amount of hair per examination area was reduced by 89%, whereas in nearly 70% of the remaining hair a complete depigmentation occurred, and in more than 95% of the women the remaining hair substantially decreased in thickness, thus becoming very fine. The results were identical for both cream preparations, thereby both showing the same biological effectiveness.

Same effects could be detected in 6 women having so-called "facial hair on the chin and upper lip of women" by the application of a cream having the composition according to Example 13:

It is postulated that the selected combination of active substances results in a suppression of both the local estradiol and the local dihydrotestosterone generation, and, moreover, the possible effect of the circulating dihydrotestosterone in the hair papilla is blocked via blocking of the androgen receptors, for example based on the effects of the saw palmetto extract.

The invention claimed is:

1. A composition for regulating hair growth, the composition consisting essentially of:
   i) a combination of active components (A) and (B), wherein (A) is at least one chemical-synthetic steroidal aromatase inhibitor that inhibits aromatase by covaient binding of the aromatase, wherein the chemical-synthetic aromatase inhibitor is 4-hydroxy-androstenedione or a 4-carboxylic acid ester derivative thereof; and (B) is an extract of saw palmetto (*Serenoa serrulata* fruit extract) that contains one or more active components selected from the group consisting of 5α reductase type I and/or type II inhibitors and androgen receptor blockers, and wherein the extract has at least 90% by weight of phytosterols and/or flavonoids; and
   ii) at least one suitable carrier, excipient or additive selected from the group consisting of: water, dimethyl isosorbide, *urtica dioica* (nettle) extract, *tussilago farfara* (coltsfoot) leaf extract, retinyl palmitate, tocopherol, zinc pca, *equisetum arvense* extract, *malva sylvestris* (mallow) extract, disodium cystinyl disuccinate, piroctone olamine, tridecyl sallcylate, niacinamide, *hamamelis virginiana* (witch hazel) extract, *olea europaea* (olive) oil unsaponifiables, biotin, urea, peg-40 hydrogenated castor oil, propylene glycol, lactic acid, denatured alcohol (70%), *persea gratissima* (avocado oil), octyldodecanol, C12-13 alkyl lactate, cetearyl isononanoate, caprylic/capric triglyceride, polyglyceryl-3 methylglucosedistearate, ammonium acryloyidimethyltaurate/vp copolymer, tocopheryl acetate, capryloyl glycine, tribehenin, glycerin, xylitol, sorbitol, paimatine, coco-glucoside, ethyihexylglycerin, sorbitan laurate, poloxamer, nylon-12, lecithin, ascorbyl palmitate, ammonia, phenoxyethanol, and xanthan gum, and wherein said composition is in the form of a cream, a gel, or an emulsion.

2. The composition according to claim 1, wherein the saw palmetto extract is an ethanol extract of saw palmetto fruits.

3. The composition according to claim 1, wherein the chemical-synthetic aromatase inhibitor 4-acetoxy-androstene-dione.

4. A composition for regulating hair growth, the composition consisting essentially of:
   i) a combination of active components (A) and (B), wherein (A) is an aromatase inhibiting extract of rapeseed comprising steroidal aromatase inhibitors obtained by ethanol extract of rapeseeds; and (B) is an extract of saw palmetto (*Serenoa serrulata* fruit extract) that contains one or more active compounds selected from the group consisting of 5α reductase type I and/or type II inhibitors and androgen receptor blockers, and wherein the saw palmetto extract has at least 90% by weight of phytosterols and/or flavonoids; and
   ii) at least one suitable carrier, excipient or additive selected from the group consisting of: water, dimethyl isosorbide, *urtica dioica* (nettle) extract, *tussilago farfara* (coltsfoot) leaf extract, retinyl palmitate, tocopherol, zinc pca, *equisetum arvense* extract, *malva sylvestris* (mallow) extract, disodium cystinyl disuccinate, piroctone olamine, tridecyl salicylate, niacinamide, *hamamelis virginiana* (witch hazel) extract, *olea europaea* (olive) oil unsaponifiables, biotin, urea, peg-40 hydrogenated castor oil, propylene glycol, lactic acid, and denatured alcohol, and wherein said composition is in the form of a cream, a gel, or an emulsion.

5. A composition or regulating har growth, the composition consisting essentially of:
   i) a combination of components (A) and (B) as active substances, wherein (A) is an aromatase inhibiting extract of soya beans comprising steroidal aromatase inhibitors obtained by extracting soya beans with ethanol; and (B) is an extract of saw palmetto (*Serenoa serrulata* fruit extract) that contains one or more active ingredient substances selected from the group consisting of 5α reductase type I and/or type II inhibitors and androgen receptor blockers, and wherein the saw palmetto extract has at least 90% by weight of phytosterols and/or flavonoids; and
   ii) at least one suitable, carrier, excipient or additive selected from the group consisting of: water, dimethyl isosorbide, *urtica dioica* (nettle) extract, *tussilago farfara* (coltsfoot) leaf extract, retinyl palmitate, tocopherol, zinc pca, *equisetum arvense* extract, *malva sylvestris* (mallow) extract, disodium cystinyl disuccinate, piroctone olamine, tridecyl salicylate, niacinamide, *hamamelis virginiana* (witch hazel) extract, *olea europaea* (olive) oil unsaponifiables, biotin, urea, peg-40 hydrogenated castor oil, propylene glycol, lactic acid, and denatured alcohol, and wherein said composition is in the form of a cream, a gel, or an emulsion.

6. A composition for regulating hair growth, the composition consisting essentially of:
   i) a combination of components (A) and (B) as active substances. wherein (A) is an aromatase inhibiting extract of rapeseed comprising steroidal aromatase inhibitors and an aromatase inhibiting extract of soya beans comprising steroidal aromatase inhibitors, wherein the extracts are obtained by extracting rapeseed and the soya beans with alcohol; (B) an extract of saw palmetto (*Serenoa serrulata* fruit extract) that contains one or more active ingredient substances selected from the group consisting of 5α reductase type I and/or type II inhibitors and androgen receptor blockers, and wherein the saw palmetto extract has at least 90% by weight of phytosterols and/or flavonoids; and
   i) at least one suitable carrier, excipient or additive selected from the group consisting of: water, dimethyl isosorbide, *urtica dioica* (nettle) extract, *tussilago farfara* (coltsfoot) leaf extract, retinyl palmitate, tocopherol, zinc pca, *equisetum arvense* extract, *malva syl-*

*vestris* (mallow) extract, disodium cystinyl disuccinate, piroctone olamine, tridecyl salicylate, niacinamide, *hamamelis virginiana* (witch hazel) extract, *olea europaea* (olive) oil unsaponifiables, biotin, urea, peg-40 hydrogenated castor oil, propylene glycol, lactic acid, and rest denatured alcohol (70%), *persea gratissima* (avocado oil), octyidodecanol, C12-13 alkyl lactate, cetearyl isononanoate, caprylic/capric triglyceride, polyglyceryl-3 methylglucosedistearate, ammonium acryloyidimethyltaurate/vp copolymer, tocopheryl acetate, capryloyl glycine, tribehenin, glycerin, xylitol, sorbitol, palmatine, coca-glucoside, ethylhexylglycerin, sorbitan laurate, poloxamer, nylon-12, lecithin, ascorbyl palmitate, ammonia, phenoxyethanol, and xanthan gum, and wherein said composition is in the form of a cream, a gel, or an emulsion.

\* \* \* \* \*